(12) United States Patent
Bitter et al.

(10) Patent No.: US 8,044,353 B2
(45) Date of Patent: Oct. 25, 2011

(54) NON-DISPERSIVE INFRARED GAS ANALYZER

(75) Inventors: Ralf Bitter, Karlsruhe (DE); Camiel Heffels, Stutensee-Büchig (DE); Thomas Hörner, Karlsruhe (DE); Ludwig Kimmig, Ettlingen (DE); Martin Kionke, Karlsruhe (DE); Michael Ludwig, Karlsruhe (DE)

(73) Assignee: Siemens Aktiengesellschaft, München (DE)

( * ) Notice: Subject to any disclaimer, the term of this patent is extended or adjusted under 35 U.S.C. 154(b) by 0 days.

(21) Appl. No.: 12/867,859

(22) PCT Filed: Feb. 15, 2009

(86) PCT No.: PCT/EP2009/051743
§ 371 (c)(1),
(2), (4) Date: Oct. 26, 2010

(87) PCT Pub. No.: WO2009/101197
PCT Pub. Date: Aug. 20, 2009

(65) Prior Publication Data
US 2011/0032514 A1    Feb. 10, 2011

(30) Foreign Application Priority Data
Feb. 15, 2008    (DE) .......................... 10 2008 009 189

(51) Int. Cl.
*G01J 5/00*    (2006.01)
(52) U.S. Cl. .................................................. 250/338.1
(58) Field of Classification Search .......... 250/330–335, 250/336.1–336.2, 337, 338.1–338.5, 339.01–339.16, 250/340, 341.1–341.8, 344, 345
See application file for complete search history.

(56) References Cited

U.S. PATENT DOCUMENTS 2,924,713 A    2/1960    Liston
(Continued)

FOREIGN PATENT DOCUMENTS

| DE | 1 109 418 | 6/1961 |
|---|---|---|
| DE | 1 204 430 | 11/1965 |
| DE | 2 332 288 | 1/1974 |
| DE | 2 400 221 | 7/1975 |

(Continued)

OTHER PUBLICATIONS

Jacek et al., "Frequency characteristic of an optopneumatic detector," 2006, Molecular and Quantum Acoustics, vol. 27, pp. 141-147.*

*Primary Examiner* — Kiho Kim
(74) *Attorney, Agent, or Firm* — Cozen O'Connor

(57) ABSTRACT

The invention relates to a NDIR-gas analyser comprising an infrared radiation source (1), a measuring vessel (3) containing a gas mixture (4) having a measuring gas component (5) that is to be detected, and a detector device (7) that is arranged behind the measuring vessel that can detect the influence of ageing of the radiation source (1) and optionally dirt deposits in the optical radiation path without interrupting measuring. According to the invention, at least one optopneumatic detector (15) is arranged in the beam path of the radiation source (1), said detector being filled with any gas (16) when arranged between the radiation source (1) and the measuring vessel (3). The concentration of measuring gas components is lower in the detector (15) than in the measuring vessel (3) if filled with the measuring gas components, and said detector is filled with a gas when arranged between the measuring vessel (3) and the detector device (7), the absorption spectrum of the detector being outside of the spectrum of the measuring gas components (5) and other transversal gases in the gas mixture (4). The measuring signal (12) of the detector device (7) is corrected by the detector signal (21) generated by the detector (15).

2 Claims, 5 Drawing Sheets

U.S. PATENT DOCUMENTS

| | | | |
|---|---|---|---|
| 3,215,832 A | | 11/1965 | Madsen et al. |
| 3,770,974 A | | 11/1973 | Fertig |
| 3,953,734 A | | 4/1976 | Dimeff |
| 3,968,370 A | | 7/1976 | Luft |
| 4,355,233 A | * | 10/1982 | Warnke et al. ................. 250/343 |
| 4,467,435 A | * | 8/1984 | Warnke et al. ................... 702/24 |
| 5,321,266 A | | 6/1994 | Weinel |
| 2008/0011952 A1 | * | 1/2008 | Fabinski et al. ............... 250/344 |

FOREIGN PATENT DOCUMENTS

| | | |
|---|---|---|
| DE | 26 38 522 | 3/1978 |
| DE | 35 29 482 | 2/1987 |
| DE | 9 014 162 | 12/1990 |
| DE | 44 03 763 | 8/1995 |
| DE | 195 40 489 | 4/1997 |
| DE | 10 2004 007 953 | 9/2005 |

* cited by examiner

NON-DISPERSIVE INFRARED GAS ANALYZER

CROSS-REFERENCE TO RELATED APPLICATIONS

This is a U.S. national stage of International Application No. PCT/EP2009/051743, filed on 15 Feb. 2009. Priority is claimed on German Application No. 10 2008 009 189.8, filed on 15 Feb. 2008. The entire content of both applications are incorporated herein by reference.

BACKGROUND OF THE INVENTION

1. Field of the Invention

The invention relates to a non-dispersive infrared (NDIR) gas analyzer for verifying a measuring gas component in a gas mixture, having an infrared radiation source for generating an infrared radiation, a modulation device for modulating the infrared radiation, a measuring vessel containing the gas mixture and being irradiated by the modulated infrared radiation and a detector device arranged behind the measuring vessel in the radiation direction, where the detector device supplies a measuring signal which corresponds to the concentration of the measuring gas component in the gas mixture.

2. Description of the Related Art

Single-beam and two-beam NDIR gas analyzers are known. With single-beam devices, the infrared radiation generated by the infrared emitter is routed after modulation, such as by a rotating diaphragm wheel, through the measuring vessel containing the gas mixture with the measuring gas component to the detector device. With two-beam devices, the infrared radiation is subdivided into a modulated measuring radiation passing through the measuring vessel and into an inversely-phased modulated comparison radiation passing through a comparison vessel filled with a comparison gas. Optopneumatic detectors filled with the gas components to be verified and comprising one or more receiver chambers arranged adjacent or to the rear of one another are usually used for the detector device.

To ensure functional reliability, NDIR gas analyzers must be able to diagnose certain faults, depending on the level of safety requirement to rule out faulty measurements. The quantitative analysis of the components of an NDIR gas analyzer shows that the infrared radiation source has the highest error rate. This component is subjected to a slow but consistent ageing.

DE 35 29 482 A1 discloses a two-beam NDIR gas analyzer. Here, a further flow or pressure-sensitive sensor is arranged in a cable assembly connecting the receiver chambers in the measuring and comparison radiation path to monitor the full functionality of the gas analyzer calibrated to zero and to exclude long-term drifts of the zero point which occur as a result of the emitter ageing or window dirt, where the sensor generates a further detector signal which is proportional to the overall intensity of the detected infrared radiation. With this further signal, the functionality of the gas analyzer can also be monitored in cases of zero compensation of the gas analyzer, if, in other words, the measuring signal is zero. The further signal can be used as an input variable for regulating the infrared radiation source, whereby the radiation output is regulated such that this signal always remains constant, i.e., in cases of zero compensation, the system always has a constant sensitivity, since the influence of the emitter ageing and dirt deposits in the optical radiation path is compensated by the regulation. The otherwise necessary calibration with calibration gas at certain intervals can thus be avoided.

In contrast, with single-beam devices, a regular calibration with calibration gas is necessary, as a result of which the availability of the gas analyzer for measurement purposes is reduced.

SUMMARY OF THE INVENTION

It is an object of the invention to detect the influence of ageing of a radiation source and if necessary of dirt deposits in an optical radiation path without interrupting measuring and in this way, in particular, without modifying the existing detector device.

This and other objects and advantages are achieved in accordance with the invention by providing at least one optopneumatic detector that is arranged in the radiation path of the infrared radiation source, where the detector is filled with any gas when arranged between the infrared radiation source and the measuring vessel, and, if filled with the measuring gas component, the concentration of the measuring gas component in the optopneumatic detector is set lower than that in the measuring vessel, and when arranged between the measuring vessel and detector device, is filled with a gas of which the absorption spectrum lies outside of the spectra of the measuring gas component and further transverse gases in the gas mixture and by providing a correction device for correcting the measuring signal of the detector device with the detector signal generated by the detector. Insofar as the gas consists of a number of gas components, in the latter case the absorption spectra of all gas components lies outside of the spectra of the measuring gas component and further transverse gases.

If the optopneumatic detector is arranged between the infrared radiation source and the measuring vessel, the detector signal generated by it is thus only influenced by the radiation intensity of the radiation source. A permanent monitoring of the infrared radiation source for dirt and ageing and a corresponding correction of the measurement result provided by the gas analyzer is possible. The optopneumatic detector can be filled with any gas, including the measuring gas component, where, in the latter case, the concentration of the measuring gas component must be lower than in the measuring vessel to keep the preabsorption for the actual measurement as low as possible.

If the optopneumatic detector is arranged between the measuring vessel and the detector device and filled with a gas of which the absorption spectrum lies outside of the spectra of the measuring gas component and if necessary of further transverse gases of the gas mixture located in the measuring vessel, the detector signal generated by the optopneumatic detector is influenced by the radiation intensity of the radiation source and the dirt in the measuring vessel. Permanent monitoring of the overall radiation path of the gas analyzer for dirt and ageing and a corresponding correction of the measuring result supplied by the gas analyzer is thus possible.

Arranging the optopneumatic detector between the infrared radiation source and the measuring vessel and furthermore between the measuring vessel and the detector device advantageously enables ageing or dirt in the radiation source and dirt in the measuring vessel to be diagnosed separately.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

BRIEF DESCRIPTION TO THE DRAWINGS

To further explain the invention, reference is made below to the in the drawings, which show different exemplary embodiments of the inventive NDIR gas analyzer, in which.

DESCRIPTION OF THE PREFERRED EMBODIMENTS

Figure 1:
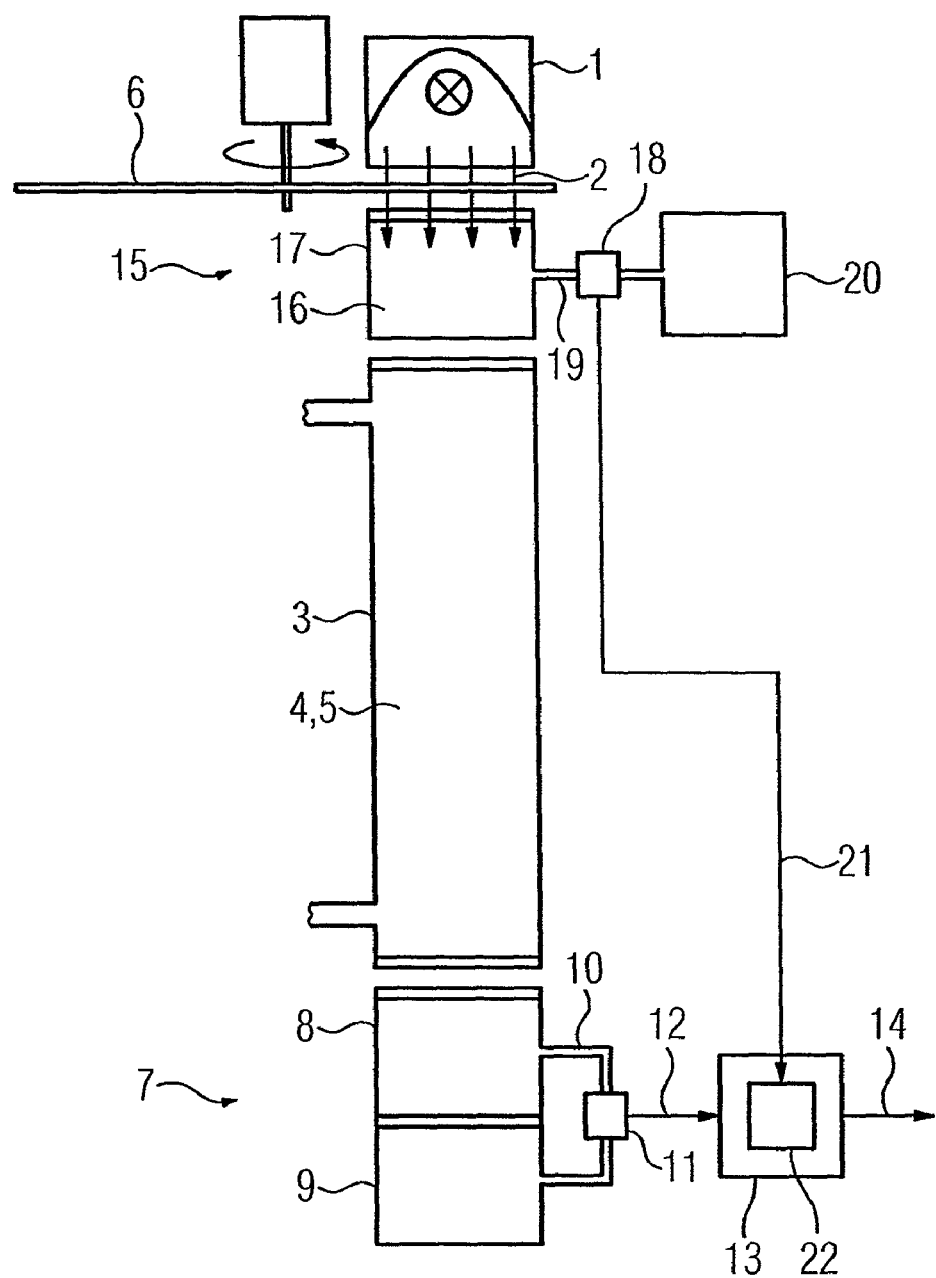
FIG. 1 is a schematic illustration of a single-beam NDIR gas analyzer in accordance with an embodiment of the invention.

FIG. 1 is an illustration of a schematic block diagram of a single-beam NDIR gas analyzer having an infrared radiation source 1, which generates an infrared radiation 2. The infrared radiation 2 irradiates a measuring vessel 3, which contains a gas mixture 4 with a measuring gas component 5, the concentration of which is to be determined. Here, the infrared radiation 2 is pre-modulated by a modulation device 6 arranged between the infrared radiation source 1 and the measuring vessel 3 which comprises, for example a rotating diaphragm wheel. After irradiating the measuring vessel 3, the infrared radiation 2 strikes a detector device 7, which, in the exemplary embodiment shown here, comprises a two-layer receiver comprising two receiver chambers 8, 9 arranged one behind the other and filled with the measuring gas component 5 or a substitute gas, which are connected to one another by a connecting line 10 with a pressure or flow-sensitive sensor 11 arranged therein. The sensor 11 generates a measuring signal 12, from which the concentration of the measuring gas component 5 in the gas mixture 4 is determined in an evaluation device 13 as a measuring result 14.

To determine the intensity of the infrared radiation radiated into the measuring vessel 3, an optopneumatic detector 15 comprising a single-layer receiver is inserted between the infrared radiation source 1 (behind the modulation device 6) and the measuring vessel 3. The optopneumatic detector 15 consists of a receiver chamber 17 filled with any gas 16 (such as the measuring gas component 5 in a lower concentration than in the measuring vessel 3), where the receiver chamber is connected to a compensation chamber 20 outside of the radiation path of the infrared radiation 2 by a connecting line 19 with a pressure or flow-sensitive sensor 18 arranged therein. The pressure or flow-sensitive sensor 18 generates a detector signal 21, which represents the intensity of the infrared radiation 2 reaching the measuring vessel 3 and with which the measuring signal 12 of the detector device 7 is corrected inside the evaluation device 13 in a correction device 22, so that the measuring result 14 is independent of intensity changes in the infrared radiation 2, for instance as a result of ageing or dirt in the radiation source 1.

Figure 2:
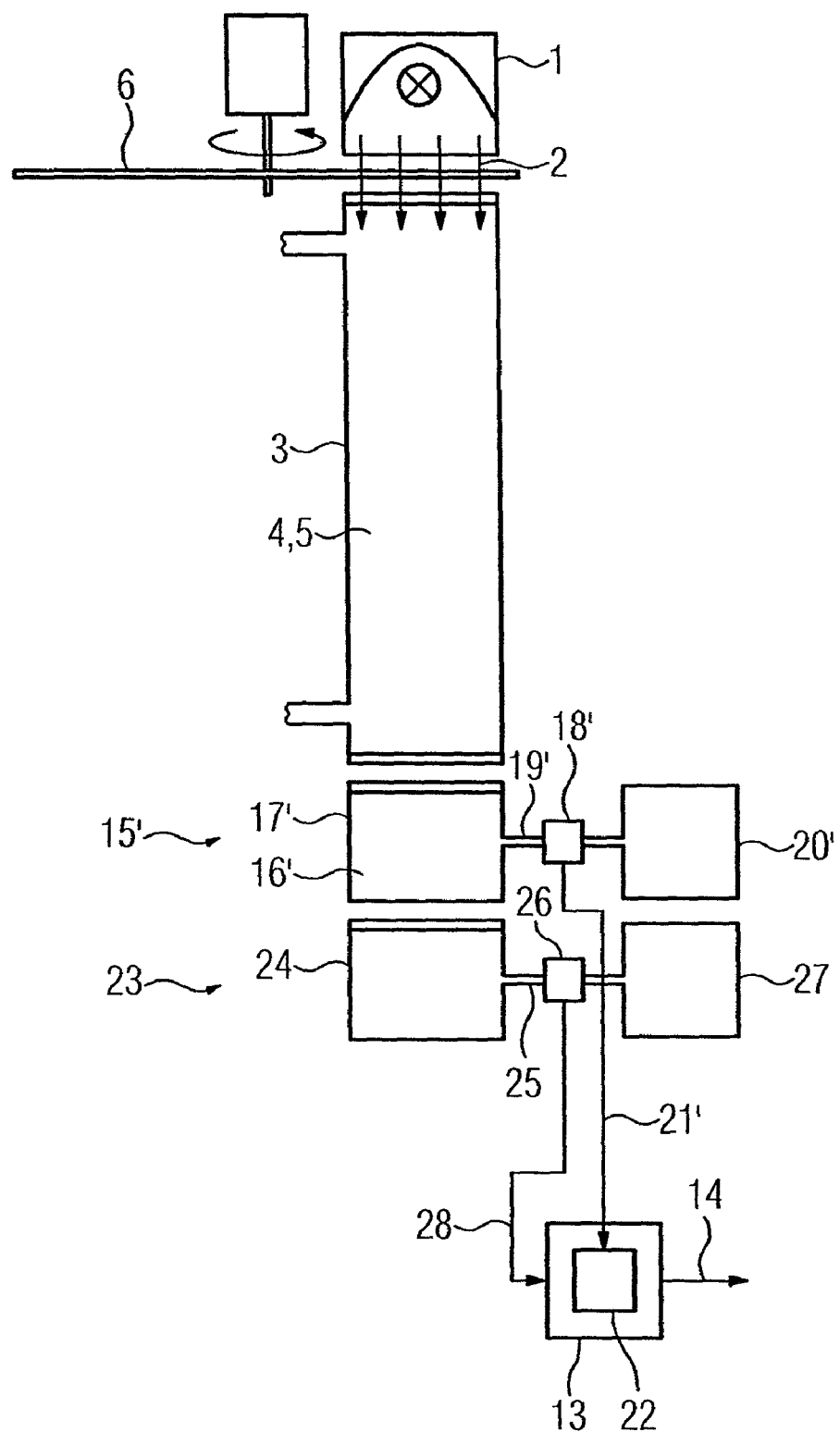
FIG. 2 is a schematic illustration of a single-beam NDIR gas analyzer of FIG. 1 in accordance with an alternative embodiment.

The NDIR gas analyzer shown in FIG. 2 differs from that of FIG. 1 in that the optopneumatic detector 15' is arranged between the measuring vessel 3 and the detector device 23 and includes a receiving chamber 17' filled with a gas 16', the absorption spectrum of which lies outside of the spectra of the measuring gas component 5 and further transverse gases in the gas mixture 4 to be analyzed. As a result, intensity changes in the infrared radiation 2 are detected and compensated, which are not only caused by the ageing or dirt in the radiation source 1 but instead also by dirt in the measuring vessel 3. The detector device 23 can comprise a two-layer receiver, as shown in the example in FIG. 1, or a single-layer receiver, as shown in FIG. 2. Here, a receiver chamber 24 filled with the measuring gas component 5 or a substitute gas is connected to a compensation chamber 27 outside of the radiation path of the infrared radiation 2 by a connecting line 25 with a pressure or flow-sensitive sensor 26 arranged therein. Conversely, in the example of FIG. 1, the detector device 7 can also comprise a single-layer receiver.

Figure 3:
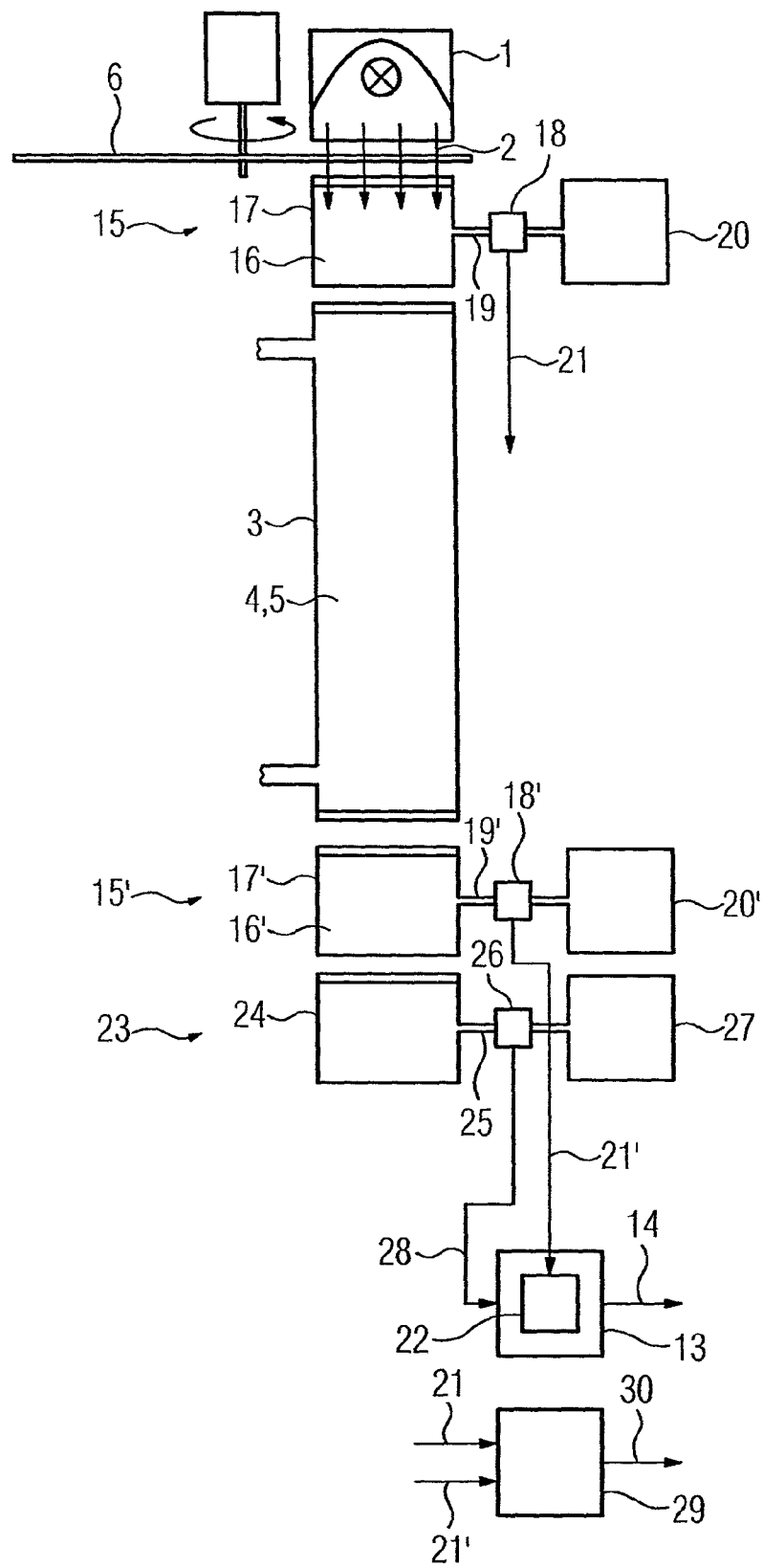
FIG. 3 is a schematic illustration of a single-beam NDIR gas analyzer of FIG. 2 in accordance with another embodiment of the invention.

The exemplary embodiment depicted in FIG. 3 differs from that of FIG. 2 in that in addition to the optopneumatic detector 15' between the measuring vessel 3 and the detector device 23, provision is also made for the optopneumatic detector 15 shown in FIG. 1 between the infrared radiation source 1 and the measuring vessel 3. The detector signals 21, 21' of both optopneumatic detectors 15, 15' are fed to an evaluation device 29, which separately diagnoses ageing or dirt in the radiation source 1 and measuring vessel 3 from both detector signals 21, 21' (diagnosis information 30).

Figure 4:
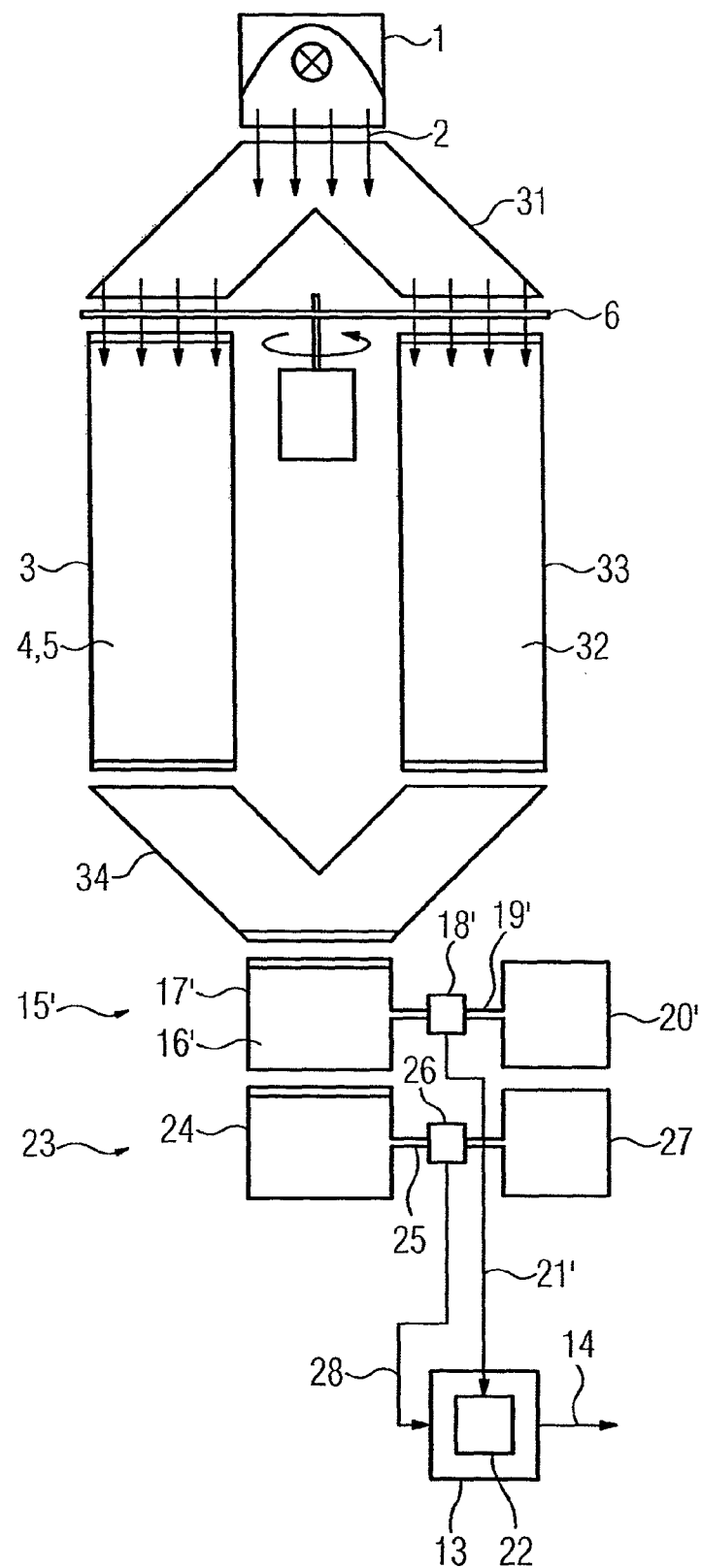
FIG. 4 is a schematic illustration of a single beam NDIR gas analyzer of FIG. 3 in accordance with another embodiment of the invention.

The NDIR gas analyzer shown in FIG. 4 differs from that shown in FIG. 2 in that here the NDIR gas analyzer has a two-beam configuration. A beam splitter 31 divides the infrared radiation 2 generated by the infrared emitter 1 onto a measuring radiation path through the measuring vessel 3 containing the gas mixture 4 with the measuring gas component 5, and onto a comparison radiation path through a comparison vessel 33 filled with a comparison gas 32. The measuring radiation path and the comparison radiation paths are rejoined behind the measuring vessel 3 and the comparison vessel 33 by a radiation collector 34, and then reach the arrangement of the optopneumatic detector 15' and the detector device 23 as previously described with reference to FIG. 2.

In the exemplary embodiments shown, other detector systems are contemplated instead of the two-layer receiver 7 or the single-layer receiver 23.

Figure 5:
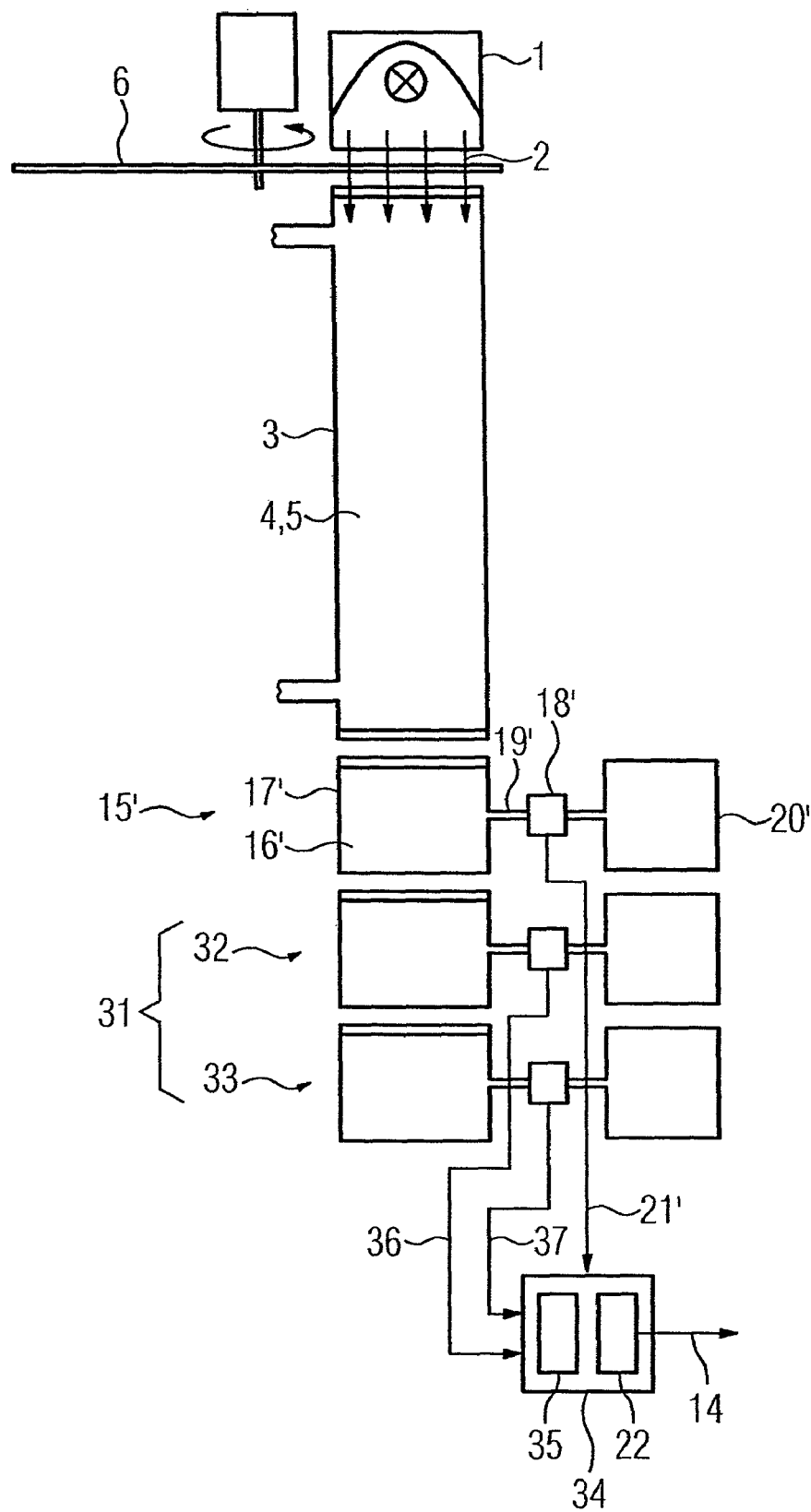
FIG. 5 is a schematic illustration of an NDIR gas analyzer in accordance with another embodiment of the invention.

As shown in FIG. 5, in addition to a first single-layer receiver 32 containing the measuring gas component, the detector device 31 can comprise at least one further single-layer receiver 33 lying in the radiation path, which contains a transverse gas. The evaluation device 34 contains an n-dimensional calibration matrix 35 which corresponds to the number n of single-layer receivers, in which calibration matrix, measuring signal values obtained in the case of different known concentrations of the measuring gas component 5 in the presence of different known transverse gas concentrations are stored as n-tuples. When measuring unknown concentrations of the measuring gas component 5 in the presence of unknown transverse gas concentrations, the concentration of the measuring gas component 5 in the gas mixture 4 is determined by comparing the n-tuples of measuring signal values 36, 36 obtained thereby with the n-tuples of measuring signal values stored in the calibration matrix 35.

Thus, while there are shown, described and pointed out fundamental novel features of the invention as applied to preferred embodiments thereof, it will be understood that various omissions and substitutions and changes in the form and details of the illustrated apparatus, and in its operation, may be made by those skilled in the art without departing from the spirit of the invention. Moreover, it should be recognized that structures shown and/or described in connection with any disclosed form or embodiment of the invention may be incorporated in any other disclosed or described or suggested form or embodiment as a general matter of design choice.

The invention claimed is:

1. A non-dispersive infrared gas analyzer for verifying a measuring gas component in a gas mixture, comprising: an infrared radiation source for generating an infrared radiation; a modulation device for modulating the infrared radiation; a measuring vessel containing the gas mixture and irradiated by the modulated infrared radiation; a detector device arranged behind the measuring vessel in the radiation direction, the detector device providing a measuring signal which corresponds to a concentration of the measuring gas component in the gas mixture; at least one optopneumatic detector arranged in the radiation path of the infrared radiation source, wherein when the at least one optopneumatic detector is arranged between the infrared radiation source and the measuring vessel being filled with any gas, and when the at least one optopneumatic detector is filled with the measuring gas component, then the concentration of the measuring gas component in the optopneumatic detector is lower than the concentration of the measuring gas in the measuring vessel, and when the at least one optopneumatic detector is arranged between the measuring vessel and the detector device, then the optopneumatic detector is filled with a gas having an absorption spectrum outside of a spectra of the measuring gas component and further interferent gases in the gas mixture; and a correction device for correcting the measuring signal of the detector device with a detector signal generated by the optopneumatic detector.

2. The non-dispersive infrared gas analyzer as claimed in claim 1, wherein the at least one optopneumatic detector includes a first optopneumatic detector arranged between the infrared radiation source and the measuring vessel and a second optopneumatic detector arranged between the measuring vessel and the detector device, detector signals of both the first and second optopneumatic detectors are fed to an evaluation device which diagnoses ageing or dirt in the radiation source and the measuring vessel from the detector signals of the first and second optopneumatic detectors.

* * * * *